(12) United States Patent
Dasari et al.

(10) Patent No.: US 11,549,081 B2
(45) Date of Patent: Jan. 10, 2023

(54) METHOD TO DESTABILIZE EMULSION FEEDSTOCKS FOR THE RECOVERY OF VALUABLE PRODUCTS

(71) Applicant: RRIP, LLC, Pleasant Hill, IA (US)

(72) Inventors: Mohan Prasad A. Dasari, West Des Moines, IA (US); Hugh Tallant Warren, Des Moines, IA (US)

(73) Assignee: RRIP, LLC, Pleasant Hill, IA (US)

(*) Notice: Subject to any disclaimer, the term of this patent is extended or adjusted under 35 U.S.C. 154(b) by 666 days.

(21) Appl. No.: 15/479,734

(22) Filed: Apr. 5, 2017

(65) Prior Publication Data
US 2017/0298293 A1    Oct. 19, 2017

Related U.S. Application Data

(63) Continuation-in-part of application No. 15/131,133, filed on Apr. 18, 2016.

(51) Int. Cl.
| | | |
|---|---|---|
| *C11B 13/00* | (2006.01) | |
| *C11B 13/02* | (2006.01) | |
| *C07C 227/28* | (2006.01) | |
| *C11B 3/00* | (2006.01) | |
| *C11B 11/00* | (2006.01) | |

(Continued)

(52) U.S. Cl.
CPC ............. *C11B 13/00* (2013.01); *A23J 7/00* (2013.01); *A23K 20/174* (2016.05); *C07C 29/095* (2013.01); *C07C 29/76* (2013.01); *C07C 213/08* (2013.01); *C07C 213/10* (2013.01); *C07C 227/28* (2013.01); *C07C 227/40* (2013.01); *C11B 3/00* (2013.01); *C11B 7/00* (2013.01);

(Continued)

(58) Field of Classification Search
CPC . C11B 3/04; C11B 3/00; C11B 13/005; C11B 13/04; C11B 13/00; C11B 3/06
See application file for complete search history.

(56) References Cited

U.S. PATENT DOCUMENTS

| | | | | |
|---|---|---|---|---|
| 2,758,122 A | * | 8/1956 | Clayton | C11B 13/00 552/545 |
| 5,210,242 A | * | 5/1993 | Asbeck | C11B 13/02 554/188 |

(Continued)

OTHER PUBLICATIONS

Dowd, JAOCS, 73(10): 1287-1295, 1996. (Year: 1996).*

*Primary Examiner* — Allison M Fox
*Assistant Examiner* — Qing Xu
(74) *Attorney, Agent, or Firm* — Brick Gentry Law Firm; Brian J. Laurenzo; Jessica L. Susie

(57) ABSTRACT

Provided are methods to destabilize emulsion feedstocks. In the methods, a moderate temperature is applied to the feedstock to create a first mixture. The moderate temperature may be between 120 and 220 degrees Celsius. The first mixture is mixed at the moderate temperature, such as by staged mixing in some embodiments. Moreover, the first mixture is retained at the moderate temperature for up to six hours. The first mixture is separated into an oil phase, convoluted phase, and a water phase. In some embodiments, the moderate temperature may be 125 to 150 degrees Celsius, such as between 125 and 130 degrees Celsius. Moreover, the first mixture may be retained at the moderate temperature for between forty-five minutes and four hours, such as from two to four hours. The separation may occur at the moderate temperature.

33 Claims, 1 Drawing Sheet

(51) Int. Cl.
*C07C 227/40* (2006.01)
*C07C 29/76* (2006.01)
*C07C 213/10* (2006.01)
*A23K 20/174* (2016.01)
*C11B 7/00* (2006.01)
*A23J 7/00* (2006.01)
*C07C 29/09* (2006.01)
*C07C 213/08* (2006.01)

(52) U.S. Cl.
CPC ............... *C11B 11/00* (2013.01); *C11B 13/02* (2013.01); *Y02W 30/74* (2015.05)

(56) References Cited

U.S. PATENT DOCUMENTS

2011/0283602 A1* 11/2011 Gallop .................... B01D 1/00
44/307
2016/0207879 A1* 7/2016 Berry ....................... C11C 3/04

* cited by examiner

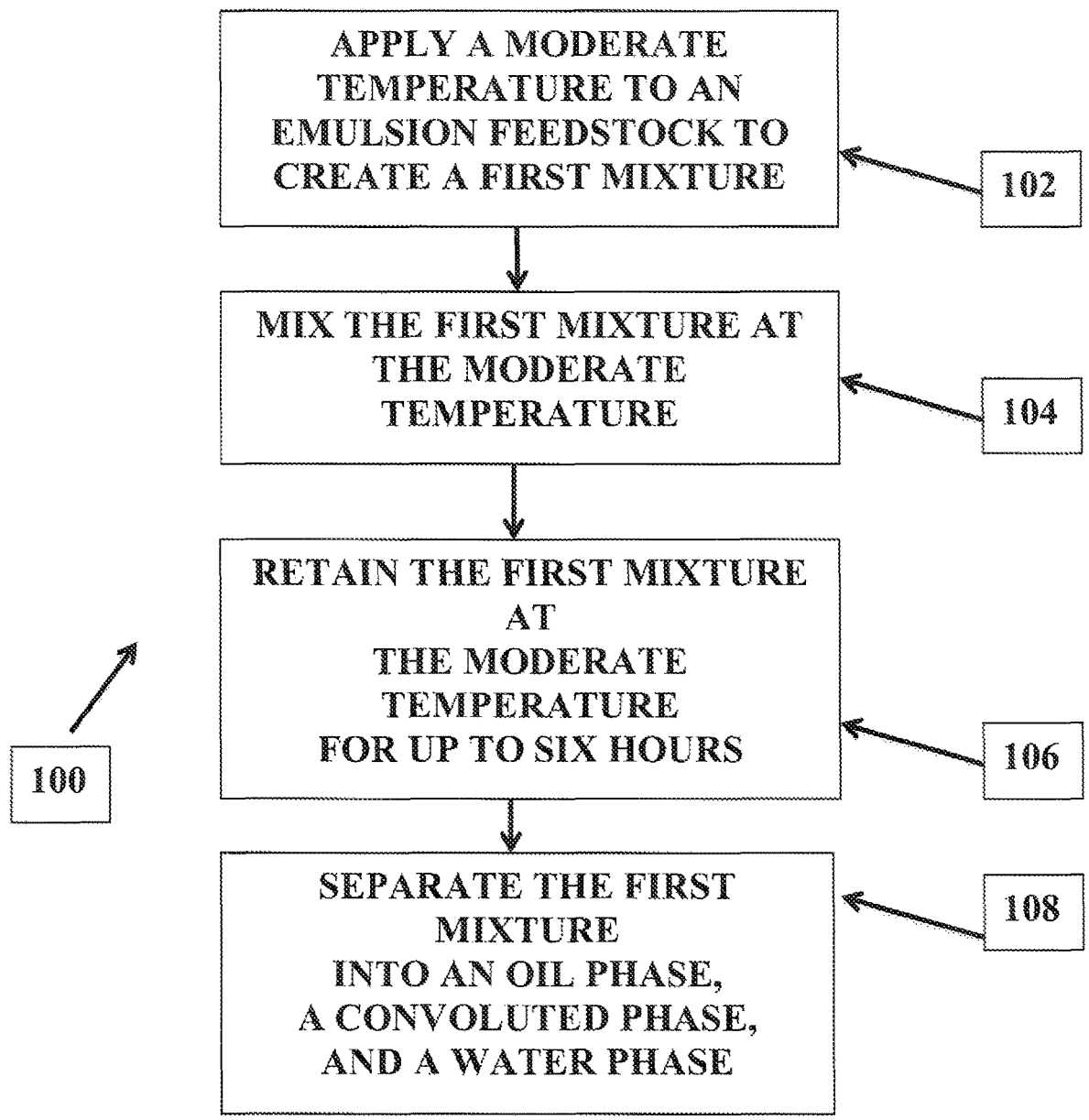

METHOD TO DESTABILIZE EMULSION FEEDSTOCKS FOR THE RECOVERY OF VALUABLE PRODUCTS

CROSS-REFERENCE TO RELATED APPLICATIONS

This application is a continuation-in-part of U.S. non-provisional patent application Ser. No. 15/131,133, filed on Apr. 18, 2016 and entitled "Method of Processing Phospholipid Based Lipid Materials". Application Ser. No. 15/131,133 is hereby incorporated by reference in its entirety.

FIELD OF THE INVENTION

This invention relates generally to the recovery of oil and other valuable products from emulsion feedstocks including, but not limited to, gums and soapstocks, by destabilizing the emulsion found in such feedstocks.

BACKGROUND

Crude vegetable oils contain triglycerides along with impurities such as free fatty acids, phospholipids, and others. The impurities are removed from the crude vegetable oil by the vegetable oil refining process. Accordingly, vegetable oil refining yields byproducts which may be further processed into valuable products. These byproducts include gums (including but not limited to dried gums, wet gums, and enzymatic wet gums), soapstocks, vegetable oil phospholipids, and others. To that end, the first step in the refining process is often degumming. Degummed oil may then be treated to remove free fatty acids. Often this is done by treating the degummed oil with alkali, which reacts with the free fatty acids present in the crude oil to form soap. The soap and other solid impurities are separated from the refined oil by centrifuging and are generally known as soapstock. Alternatively, in some oil refineries the phospholipids and soapstock are removed simultaneously. The soapstock from this alternate process is known as gummed soapstock and typically contains vegetable oil, phospholipids, water, and soap. The refined oil is further processed, while the gums, soapstock, and combinations thereof are treated as waste products. However, the gums, soapstock, and combinations thereof may also be further processed to recover valuable products.

One difficulty in processing these products, including but not limited to gums and soapstock, is the emulsion contained therein, which can decrease the recovery of valuable products. In many feedstocks, the emulsion is attributable to emulsifiers such as phospholipids, soaps, and proteins. Regarding phospholipids, as is known in the art, the phosphate group in the phospholipid is polar, while the fatty acid group is non-polar. Therefore, phospholipids may bind to both water and oil, thus creating the emulsion. An ideal method to break emulsions in gums, and therefore extract oil, is hydrolyzing the phospholipids to ultimately result in products such as glycerolphosphates, free fatty acids, lysophospholipids, and denatured protein. Previous methods use acid to catalyze this reaction. More specifically, traditional processing of gums uses large amounts of strong mineral acid (e.g. sulfuric acid) and extended settling times (upwards of 96 hours) to break the emulsion to recover valuable products. Furthermore, soapstock is often processed by acidulating the soapstock to recover free fatty acids and acylglycerides. The acidulation process also uses large amounts of strong mineral acid (e.g. sulfuric acid) and extended settling times (upwards of 96 hours) to break the emulsion to recover valuable products, yet in some circumstances the emulsion may not break and recovery of the valuable products is not achievable.

Feedstocks, including but not limited to gums and soapstocks, are generally inconsistent in their composition. Not only are the feedstocks from plant to plant quite different, but often, the byproduct feedstock(s) from a particular processing plant will be inconsistent over time. Therefore, it can be difficult to efficiently process feedstocks from different sources in a single facility or using a single process. Moreover, the variations in the feedstocks result in variations of the output during processing, which leads to further inefficiencies. With all emulsion feedstocks there is a wide range of compositions and rheological behaviors. Due to this range, the application of traditional processing has very low predictability on yields. The recovery is dependent on the emulsion feedstock characteristics. The dynamics of processing continuously change, and a static system like traditional processing does not offer the ability to reliably recover valuable product streams. The production of convoluted phases (not the target phase and discussed below) is extensive due to the above problems.

Accordingly, needed in the art is a process to efficiently process emulsion feedstock byproducts. Such byproducts may come from sources including, but not limited to, oil refining, oil processing, biodiesel industries, meat processing, rendering plants, food production facilities and other facilities and industries where oils and fats are in touch with water. The emulsion feedstocks may include, but are not limited to, gums and soapstocks and off-spec or expired food products. The method should reduce or eliminate the traditional change in pH necessary to process these feedstocks. Moreover, the method should be quick and also address the issues associated with the wide variety of feedstock compositions and rheological behaviors. The method should lead to clean separation of the resulting phases from which valuable products may be effectively recovered.

SUMMARY OF THE INVENTION

Provided is a method to destabilize emulsion feedstocks wherein a moderate temperature between 120 degrees Celsius and 220 degrees Celsius is applied to the feedstock to create a first mixture. The first mixture is mixed and retained at the moderate temperature for up to six hours. The first mixture is then separated into an oil phase, a convoluted phase, and a water phase. The emulsion feedstock may be selected from soapstock, gums, and combinations thereof. Moreover, at least one of a catalyst and a reactant may be added to the feedstock and the moderate temperature may be applied to the feedstock and the at least one of said catalyst and reactant to create the first mixture. The at least one of a catalyst and a reactant may be an acid. The moderate temperature may be between 125 and 150 degrees Celsius, such as between 125 and 130 degrees Celsius. Moreover, the first mixture may be retained at the moderate temperature for between forty-five minutes and four hours, such as between two and four hours. In addition, the pressure may be between 60 and 400 psig. The mixing may be staged mixing.

Separation may occur by pressurized decantation, membrane separation, centrifugation, gravity, and combinations thereof. The oil phase may include at least one of free fatty acids, acylglycerols, and phospholipids. In addition, the convoluted phase may include at least one of the desired valuable products, impurities and water, while the water phase may include at least one of hydrolyzed fractions from lipid molecules and water. Furthermore, the method of destabilizing said emulsion feedstocks may include destabilizing phospholipids.

In another embodiment, a method to destabilize emulsion feedstocks is provided which includes applying a moderate temperature between 120 and 220 degrees Celsius to said feedstock and wherein the feedstock is selected from the group consisting of gums, soapstocks, and combinations thereof. The first mixture is mixed and retained at the moderate temperature. Specifically, the first mixture may be retained at the moderate temperature for between forty-five minutes and four hours. The first mixture is separated into an oil phase, a convoluted phase, and a water phase. In some embodiments, at least one of a catalyst and a reactant is added to the feedstock and the moderate temperature is applied to the feedstock and the at least one of the catalyst and the reactant to create the first mixture. The at least one of a catalyst and a reactant may be acid. Moreover, the moderate temperature may be between 125 and 150 degrees Celsius, such as between 125 and 130 degrees Celsius. The pressure may be between 60 and 400 psig. In addition, the mixing may be staged mixing. In some embodiments separation may occur by pressurized decantation, membrane separation, centrifugation, gravity, and combinations thereof. Furthermore, the method of destabilizing emulsion feedstocks may include destabilizing phospholipids.

In yet another embodiment of the invention, a method to destabilize feedstocks including phospholipids is provided wherein a moderate temperature between 120 and 150 degrees Celsius is applied to the feedstock to create a first mixture. The feedstock is selected from the group consisting of gums, soapstocks, and combinations thereof. The first mixture is mixed at the moderate temperature. Moreover, the first mixture is retained at the moderate temperature for between two and four hours. The first mixture is then separated into an oil phase, a convoluted phase, and a water phase.

BRIEF DESCRIPTION OF THE DRAWINGS

FIG. 1 is a flow chart of an embodiment of the present invention.

DETAILED DESCRIPTION

The following is a detailed description of embodiments of a method to destabilize emulsion feedstocks for the recovery of valuable products. Accordingly, the method is applicable to feedstocks having an emulsion. Such byproducts may come from sources including, but not limited to, oil refining, oil processing, biodiesel industries, meat processing, rendering plants, and other facilities and industries where oils and fats are in touch with water. As provided above, refining fats and oils results in various byproducts which may be further processed to recover valuable products. Those byproducts include, but are not limited to, soapstocks and gums. Gums may be wet gums, dried gums, enzymatic wet gums, or another type of gum known now or in the future. Soapstocks may be any type. Gums are composed mainly of water, phospholipids, free fatty acids, and acylglycerides. In some embodiments, gums may include 40-60% water, 15-30% phospholipids, 5-15% free fatty acids, 5-15% acyglycerides, and 0-15% impurities. Soapstocks, on the other hand, are primarily composed of water, soap, phospholipids, free fatty acids, and acylglycerides. In some embodiments, soaps may include 40-60% water, 15-25% soap, 1-3% free fatty acids, 5-15% acyglycerides, and 0-15% impurities.

As discussed above, the feedstocks often include an emulsion. Due in part to the emulsion, the feedstocks also include oil which was not recovered in the initial refining processes. Accordingly, the methods of the current invention are applicable to emulsions containing suspensions of oil in solution or solution in oil. In some embodiments, the invention is applied to industrial waste byproducts from oil refining, oil processing, biodiesel industries, meat processing, rendering plants, and other facilities and industries where oils and fats are in touch with water. The byproducts may include, but are not limited to soapstocks, wet gums, and vegetable oil bottoms. In other embodiments, the invention is applied to food processing wastes and byproducts, including but not limited to mayonnaise, salad dressings, heavy cream, and butter processing wastes and byproducts. Therefore, the present invention provides for the extraction of neutral oil from emulsion feedstocks.

The invention applies moderate temperature over a limited retention time to the feedstocks to destabilize the emulsion, resulting in recoverable oils. The moderate temperature may be used in combination with other reactants and/or catalysts necessary to destabilize the emulsion in a particular feedstock. In one example, acid may be used with feedstocks containing soaps. In another example, alkali may be used with feedstocks containing free fatty acids.

Referring to FIG. 1, which is a flow chart 100 showing an embodiment of the present invention, a first step of the method is to apply moderate temperature to an emulsion feedstock to create a first mixture 102. Preferably, the moderate temperature is between 120 degrees Celsius and 220 degrees Celsius. Next, the first mixture is mixed at the moderate temperature 104, and the first mixture is retained at the moderate temperature for up to six hours. 106. Separation then occurs, resulting in an oil phase, a convoluted phase, and a water phase 108. The oil phase may include recoverable oils such as free fatty acids, acylglycerols, phospholipids, and others. The convoluted phase may include small amounts of hexane soluble fractions and water. Moreover, the water phase nay include hydrolyzed fractions from lipid molecules and water.

As discussed above, the retention time using methods of the present invention is significantly shorter than with traditional methods. Retention times of up to 6 hours are used, such as retention times of 45 minutes to 6 hours or, preferably, 2 to 4 hours. The retention time required is dependent on the emulsion feedstock being used. The retention time is intentionally short to prevent the reaction conditions from affecting the valuable components to be recovered. It is unexpected that limiting the retention time will cause reactions which destabilize the emulsion only rather than destabilizing the emulsion and degrading valuable products to be recovered.

For most feedstocks, mixing of the feedstock at the moderate temperature is preferred. Moreover, staged mixing may be employed. Overmixing the mixture may result in oil loss and poor separation. Accordingly, staged mixing drives mass transfer in the first stages of the process, which include heating and the reaction, and promotes phase separation in the later stages. In traditional processes, one mixing parameter is used rather than staged mixing.

The mixture will separate into the three phases discussed herein. Reduction of the overall processing time may be accomplished using pressurized decantation, membrane separation, or centrifugation. However, any separation means known in the art, now or in the future may be used. Under moderate temperatures, the kinematic viscosities of the separating phases differs more greatly, which allows the two primary phases of oil and solution to be more easily removed. In addition, increased pressure tends to increase oil recovery.

For some feedstocks, further processing and/or reactions will be desired. For example, in some embodiments a moderate pressure of 60-400 psig may be used. Such pressures help to maintain the liquid phase while also aiding in phase separation. Moreover, moderate pressure helps with controls. In addition, in some embodiments it may be desirable to add at least one of a reactant and a catalyst to the feedstock. In some embodiments this substance may be an acid. Depending on the composition of the feedstock, acid may react with one or more constituents of the feedstock. For other feedstocks, acid may act as a catalyst which enhances or speeds a reaction and/or phase separation. In all cases, the acid requirements are much lower using methods of the current invention, as the moderate temperature may serve the same purpose as some amounts of the acid, particularly if acid is a catalyst. For example, in some circumstances, the acid requirement may be zero. In other circumstances, the acid requirement may be 50-75% less than with traditional methods.

The application of moderate temperature over a limited time to destabilize emulsions is a unique and unexpected invention. Specifically, controlling the temperature and exposure to the temperature results in destabilizing the emulsion but does not affect the valuable products to be recovered as would be expected when increased temperatures are employed. Rather, surprisingly, recovery of the valuable byproducts is significantly increased. The particular temperature, generally between 120 and 220 degrees Celsius, is important and will differ between feedstocks having different compositions. The temperature must be high enough to carry out the destabilization in the shortened timespan, but must also be low enough to prevent undesirable side reactions, including but not limited to hydrolysis of valuable products, such as neutral oil, and oxidation. Temperatures which are too high may also prevent the products from separating well. For most feedstocks, temperatures between 120 and 220 degrees Celsius are preferred, with 125-150 being even more preferred, and 125-130 often being best.

Moreover, moderate temperature enhances separation. Although still aided by gravity, the phase separation is less dependent on gravity than in traditional methods. In the current invention, the moderate temperatures lower the viscosity of some phases and enhance phase separation. Accordingly, phase separation is substantially faster than in traditional methods.

As discussed above, another novel aspect of this process is the decreased requirement for acid, which in some cases is zero. Traditional processes of the prior art require large amounts of strong mineral acid, which is hard on equipment and requires extra, sometimes expensive, measures for disposal. The reduction and, sometimes, elimination of acid is novel and unexpected. It is believed that the high temperature, sometimes used in conjunction with high pressure, results in greater internal energy in the system than in traditional methods using acid. The greater energy has a positive effect on both separation and reaction kinetics. Specifically, the internal energy is closer to the activation energy required for the reactions necessary to destabilize the emulsion. In some cases this reaction may be hydrolysis. Moreover, increased temperature also increases the solubility of water in the oil phase, which allows for more contact between phospholipids and water, which helps to overcome mass transfer restrictions.

Employing increased temperatures, such as the moderate temperatures of the present invention is not compatible with traditional processing methods requiring large amounts of strong mineral acid. Specifically, increasing the temperature of mineral acid increases its corrosiveness and makes the mineral acid more difficult to work with. Moreover, it is unexpected that by controlling the temperature and retention time, the only result will be destabilization of the emulsion, rather than degrading valuable products. For example, in destabilizations involving hydrolysis, it is unexpected that employing a moderate temperature for a limited time will result in hydrolysis of phospholipids only and not hydrolysis of recoverable oil, such as acylglycerols. However, in emulsions including phospholipids and acylglycerols, the reaction of the present invention tends to have higher selectivity for phospholipid hydrolysis over arcylglycerol hydrolysis. Carrying out the reactions to this level of detail is surprising, as is the enhanced separation and yield gained from methods of the present invention.

When processes of the current invention are applied to soapstocks, which are generally alkaline, retention of the soapstocks at processing conditions results in a reduction of the alkalinity. This leads to a reduced mineral acid requirement. This is due at least in part to irreversible base-catalyzed hydrolysis, which consumes the hydroxide ions. This hydrolysis is preferential for phospholipids, which cause stability in emulsions. Moreover, some soapstocks do not require acid addition to induce oil production. Rather, phase separation is thought to be induced by spontaneous hydrolysis of soaps, which releases fatty acids and forms an independent phase prior to the combination reactions occurring. The rate of this reaction is increased by the moderate temperatures and pressures. Additionally, the hydrolysis of the phospholipids into glycerophospholipids (e.g. glycerophosphocholine) valuable product which can be recovered in the water phase.

Accordingly, some particularly important aspects of novelty in the methods of the present invention include increased yield recovery of the oil phase, reduced mineral acid requirement, and shortened recovery time. The reduced acid requirement leads to less chemical treatment required to process the resulting water phase. In traditional methods, the water phase must be neutralized in light of all of the strong mineral acid. The current methods avoid some or all of this processing. For example, processing wet gums with methods of the present invention may require no acid. In addition, the reduced or eliminated acid is better for the processing equipment. The reduced acidity makes stainless and austenic grades of composite metals more available for use rather than costly materials which must be used with amounts of strong acid.

Furthermore, as discussed above, methods of the present invention result in increased consistency when used with feedstocks of varying consistency. The application of moderate temperature, and sometimes moderate pressure, results in a normalization effect on the feedstocks. The normalization provides intermediate advantages prior to and after the primary reaction vessel stage of the process. The advantages include, but are not limited to, normalization of the rheological behavior, which in turn reduces the impact of viscosity on the reaction vessels, consistent product formation following processing, narrowed pressure and temperature gradients across the system, and consistent power inputs from mechanical equipment (including but not limited to pumping, agitation, and valve actuation).

EXAMPLES 900 grams of soybean-based enzymatic wet gums were processed. The enzymatic wet gums are an emulsion feedstock having a total fatty acid content of 35 wt %, hexane soluble crude fat (HSCF) of 42%, and moisture of 55 wt % and were processed using traditional methods. This was done in a 4525 Parr stirred pressure reactor at 90 degrees Celsius and atmospheric pressure with the addition of 4 wt % sulfuric acid under 200 RPM using a 4 blade, 45 degree pitched dual turbine impeller. The product was allowed to settle for 18 hours. The mass recovery was: oil phase 180 grams, convolution phase 510 grams, and water phase 176 grams. The recovery of oil was 48 wt % of the total fat content, and the resulting pH of the material was 0.55.

In contrast, 900 grams of the same soybean-based enzymatic wet gums were processed using the same equipment at 150 degrees Celsius and 120 psig under staged mixing. Importantly, no acid was added to the reaction. As discussed above, traditional processing requires large amounts of strong mineral acid. After allowing the reaction to proceed for 2 hours of retention time, the product was cooled to 80 degrees Celsius, which took approximately 35 minutes. The product was then removed from the reaction vessel and the product phases were isolated and quantized. The mass recovery was: oil phase 342 grams, convolution phase 75 grams, and water phase 465 grams. The remaining mass was water which had condensed on the outside of the glass insert within the reactor. Total processing time was 3.5 hours. The recovery of oil was 90.5 wt % of the total fat content, and the resulting pH of the product water was 3.44.

Accordingly, the process of the present invention resulted in increased oil recovery and increased pH in a significantly shorter time.

In another example, 900 grams of the same emulsion feedstock containing soaps was processed using more traditional methods. The total fatty acid content of the feedstock was 21 wt % and moisture content was 68 wt %. pH of the feedstock was 9.40. The reaction was carried out at 90 degrees Celsius and at atmospheric pressure with 4.0 wt % sulfuric acid and 200 RPM. The resulting product phases were oil phase 109 grams, convoluted phase 330 grams, and water phase 450 grams. The remaining mass was accounted for in the reactor. The oil phase yield was 58% of the total fatty acids. The pH of the resulting material was 1.45.

In contrast, 900 grams of the emulsion feedstock containing soaps was processed using the technology provided herein with the same equipment. The reaction was carried out at 135 degrees Celsius under staged mixing for 2 hours. Moreover, 2.2 wt % sulfuric acid was added. Following the reaction, the feedstock was allowed to cool to 80 degrees Celsius and removed from the reaction vessel. The product phases were distinct and easily isolated for quantification. The mass recovery was: oil phase 200 grams, convolution phase: 25 grams, and water phase 670 grams. The remaining mass was accounted for as condensate formed on the outside of the reactor glass insert. Accordingly, the recovery of the oil phase was associated with a 99.5 wt % yield of the total fatty acids. Less than 0.5 wt % of the oil was entrained in the emulsion. The resulting pH of the water phase was 4.33.

In yet another example, 500 grams of emulsion feedstock including corn oil containing 3.6 wt % insoluble impurities and 8 wt % free fatty acids was processed using previous methods as a control. 300 grams of alkali solvent was used to neutralize the residual fatty acid content, allowing separation of the produced soaps into the alkali solvent. Using the same emulsion feedstock including corn oil as in the previous example, a control experiment was performed using previous processes. The reaction was carried out at 65 degrees Celsius under 200 RPM for one minute. Following 45 minutes of retention under gravimetric settling, the contents were removed for separation. The product was completely emulsified and convoluted. No distinct phase separation had occurred and thus no recoverable oil was produced.

In contrast, 500 grams of the same emulsion feedstock including corn oil was processed using the method of the present invention. 300 grams of alkali solvent was used to neutralize the residual fatty acid content, allowing separation of the produced soaps into the alkali solvent. The reaction was carried out at 120 degrees Celsius at 200 RPM for one minute. Retention time was 45 minutes. The product was cooled to 60 degrees Celsius and separated into product phases. 433 grams of product oil was recovered. Accordingly, separation efficiency was 98%. A minimal convoluted phase was produced, having a mass of 60 grams. A heavy solvent phase having a mass of 299 grams was recovered. Residual mass was accounted for as condensate formed on the outside of the glass insert of the reactor.

In another example, 995 grams of pork grease obtained from pork meat processing containing 9.19 wt % impurities, 0.63 wt % protein matter, and 5.0 wt % moisture was processed using the method of the present invention. Impurities in this type of fat material may contain flocculating agents meant to aid in fat separation in the vendor process. These flocculating agents, polymers and other chemicals, have tendencies to stabilize water in oil emulsions. This material was allowed to settle for 18 hours at 90 deg. C, which is a common processing method. Following heated settling in the same glass insert used with the proposed system technology, the oil did not show any distinct separation r reduction in moisture content. The material was allowed to settle for an additional 18 hours and again no clear separation was seen in the material. However, at this point the moisture had decreased in the upper layers of the material to 1.50 wt %. Further testing of deeper layers of the oil showed that the progress of moisture settling was not substantial half way down the settling vessel.

In contrast, 1000 grams of the same pork grease was processed using the technology herein. Processing was carried out at 150 degrees Celsius under staged mixing for two hours. Following mixing, the material was cooled to 80 degrees Celsius and removed from the reactor. There was clear separation of material at the bottom of the glass liner, and the bulk oil fraction on top was analyzed independent of that material. The bulk oil moisture was found to be 0.95 wt %. The bottom material was also analyzed and found to be 10.8 wt % moisture. Excluding the bottoms material, 905 grams of oil was recovered and analyzed to have a 93.7 wt % oil purity. This gives an overall recovery of 97.3 wt %.

In a further example, 1004 grams of commercially available emulsified salad dressing (Ranch dressing) was processed using traditional processing techniques. Total fatty acid content of the emulsion was analyzed to be 50.9 wt %, and moisture content was found to be 35.8 wt %. Impurities testing showed the initial emulsion had 12.3 wt % non-moisture non-fat matetial. The material was processed under atmospheric pressure at a temperature of 90 degrees Celsius. 0.4 wt % (on feedstock mass basis) sulfuric acid was added, and the contents were mixed at 200 RPM with thirty minutes' retention time. 0.4 wt % acid was chosen to allow sufficient drop in pH to approximately 1.5. Following the reaction, the products were removed from the reactor and investigated for potential oil recovery. There was no oil separation. Accordingly, the mixture was allowed to gravity settle for eighteen hours at 90 degrees Celsius. After this time, there was still no oil separation and therefore there was no oil recovery. The emulsion did not break.

In contrast, 1019 grams of commercially available emulsified salad dressing (Ranch dressing) was processed using methods of the present invention. The feedstock was processed at 150 degrees Celsius and 50 psig. Staged mixing was employed for heat-up and retention, with a retention time of two hours. Following completion of retention, the material was cooled to 80 degrees Celsius and removed from the reactor. There was clear separation of oil from the bulk. Aqueous and other solids formed at the bottom of the oil phase. 530 grams of oil was recovered having a total fatty acid content of 90.4%. The oil has a moisture content of 3.0 wt %. This gives an overall yield recovery of 92.4%.

In another example, 1001 grams of commercially available oil-egg emulsion, specifically mayonnaise, was processed using traditional processing techniques. The total fatty acid content of this emulsion was analyzed and determined to be 79.1 wt % and the moisture content found to be 8.5 wt %. Impurities testing showed the emulsion material had 6.9 wt % non-fat or moisture material. Using the same set-up as in the previous examples, the material was processed under atmospheric pressure at a temperature of 90 degrees Celsius. 0.4 wt % (on feedstock mass basis) sulfuric acid was added. The material was mixed at 200 RPM with thirty minutes' retention time. pH curves were produced to meet a final reactant mixture pH of 1.4, which is achieved with the acid percentage used in this experiment. Following the reaction, the reactant mixture was pulled from the vessel and checked for oil separation. There was oil separation and the products gravity settled at 90 degrees Celsius for eighteen hours. Following the eighteen hour settling, the oil was removed and quantified. 514 grams of oil having a moisture of 0.2 wt % was removed. This gave an overall oil recovery of 64.8 wt % of the total fatty acids.

In another example, 1014 grams of commercially available oil-egg emulsion was processed using the technology of the present invention. Specifically, 1014 grams of commercially available mayonnaise was processed. Processing was carried out at 150 degrees Celsius under staged mixing for two hours. Pressure was maintained at 50 psig. Following retention, the reactant products were cooled to 80 degrees Celsius for safe handling. There was clear separation of oil from the bulk. Aqueous and other solid impurities formed at the bottom of the oil phase. 650 grams of oil was recovered having a free fatty acid content of 3.0 wt % and MI content of 0.3 wt %, which results in a yield recovery of 84.8 wt %.

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g. attached, adhered, joined) are to be construed broadly and may include intermediate members between a connection of elements and relative movement between elements. As such, joinder references do not necessarily infer that two elements are directly connected and in fixed relation to each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method to destabilize an emulsion feedstock comprising:
applying a moderate temperature between 125 degrees Celsius and 175 degrees Celsius to said emulsion feedstock to create a first mixture;
mixing said first mixture at said moderate temperature;
retaining said first mixture at said moderate temperature for up to six hours; and
separating said first mixture into an oil phase, a convoluted phase, and a water phase;
wherein neutral oil is not hydrolyzed;
wherein no solvent is added during the applying a moderate temperature, mixing, or retaining steps; and
wherein said emulsion feedstock excludes soaps.

2. The method of claim 1 wherein said emulsion feedstock is selected from gums, other water in oil or oil in water mixtures, and combinations thereof.

3. The method of claim 1 wherein a catalyst is added to said emulsion feedstock and said moderate temperature is applied to said emulsion feedstock and said catalyst to create said first mixture.

4. The method of claim 3 wherein said catalyst is an acid.

5. The method of claim 1 wherein said moderate temperature is between 125 degrees Celsius and 150 degrees Celsius.

6. The method of claim 5 wherein said moderate temperature is between 125 degrees Celsius and 130 degrees Celsius.

7. The method of claim 1 wherein said first mixture is retained at said moderate temperature for between forty-five minutes and four hours.

8. The method of claim 7 wherein said first mixture is retained at said moderate temperature for between two hours and four hours.

9. The method of claim 1 wherein the pressure is between 60 and 400 psig during the steps of applying said moderate temperature to create said first mixture, said mixing said first mixture at said moderate temperature, and said retaining said first mixture at said moderate temperature for up to six hours.

10. The method of claim 1 wherein said mixing is staged mixing.

11. The method of claim 1 wherein said separating occurs by pressurized decantation, membrane separation, centrifugation, gravity, and combinations thereof.

12. The method of claim 1 wherein the oil phase includes at least one of free fatty acids, acylglycerols, and phospholipids, the convoluted phase includes at least one of hexane soluble fractions, fatty acids, acylglycerols, phospholipids, and water, and the water phase includes at least one of hydrolyzed fractions from lipid molecules and water.

13. The method of claim 1 wherein said method of destabilizing said emulsion feedstocks includes destabilizing phospholipids.

14. The method of claim 1 wherein said separating takes place at said moderate temperature.

15. A method to destabilize an emulsion feedstock comprising:
applying a moderate temperature between 125 degrees Celsius and 175 degrees Celsius to said emulsion feedstock to create a first mixture, wherein said emulsion feedstock excludes soaps;
mixing said first mixture at said moderate temperature;
retaining said first mixture at said moderate temperature for between forty-five minutes and four hours;
separating said first mixture into an oil phase, a convoluted phase, and a water phase;
wherein no solvent is added during the applying a moderate temperature, mixing, or retaining steps; and
wherein neutral oil is not hydrolyzed.

16. The method of claim 15 wherein a catalyst is added to said emulsion feedstock and said moderate temperature is applied to said emulsion feedstock and said catalyst to create said first mixture.

17. The method of claim 16 wherein said catalyst is an acid.

18. The method of claim 15 wherein said moderate temperature is between 125 degrees Celsius and 150 degrees Celsius.

19. The method of claim 18 wherein said moderate temperature is between 125 degrees Celsius and 130 degrees Celsius.

20. The method of claim 15 wherein the pressure is between 60 and 400 psig during the steps of applying a moderate temperature to create said first mixture, mixing said first mixture at said moderate temperature, and retaining said first mixture at said moderate temperature for between forty-five minutes and four hours.

21. The method of claim 15 wherein said mixing is staged mixing.

22. The method of claim 15 wherein said separating occurs by pressurized decantation, membrane separation, centrifugation, gravity, and combinations thereof.

23. The method of claim 15 wherein said method of destabilizing said emulsion feedstocks includes destabilizing phospholipids.

24. The method of claim 15 wherein said separating takes place at said moderate temperature.

25. A method to destabilize an emulsion feedstock including phospholipids comprising:
applying a moderate temperature between 125 degrees Celsius and 150 degrees Celsius to said emulsion feedstock to create a first mixture, wherein said emulsion feedstock excludes soaps;
mixing said first mixture at said moderate temperature;
retaining said first mixture at said moderate temperature for between two and four hours;
separating said first mixture into an oil phase, a convoluted phase, and a water phase;
wherein no solvent is added during the applying a moderate temperature, mixing, or retaining steps; and
wherein neutral oil is not hydrolyzed.

26. The method of claim 1 wherein a reactant is added to said emulsion feedstock and said moderate temperature is applied to said emulsion feedstock and said reactant to create said first mixture.

27. The method of claim 26 wherein said reactant is an acid.

28. The method of claim 15 wherein a reactant is added to said emulsion feedstock and said moderate temperature is applied to said emulsion feedstock and said reactant to create said first mixture.

29. The method of claim 28 wherein said reactant is an acid.

30. The method of claim 1 wherein said emulsion feedstock is a byproduct of oil refining, oil processing, biodiesel processing, meat processing, rendering plants, food production facilities, or combinations thereof.

31. The method of claim 1 wherein said emulsion feedstock is selected from the group consisting of gums, vegetable oil phospholipids, off-spec food products, expired food products, and combinations thereof.

32. The method of claim 31 wherein said emulsion feedstock is selected from the group consisting of wet gums, dried gums, enzymatic wet gums, and combinations thereof.

33. A method to destabilize an emulsion feedstock comprising:
applying a moderate temperature between 125 degrees Celsius and 175 degrees Celsius to said emulsion feedstock to create a first mixture;
mixing said first mixture at said moderate temperature;
retaining said first mixture at said moderate temperature for up to six hours; and separating said first mixture into an oil phase, a convoluted phase, and a water phase;
wherein neutral oil is not hydrolyzed;
wherein no solvent is added during the applying a moderate temperature, mixing, or retaining steps;
wherein said emulsion feedstock excludes soaps; and
wherein said emulsion feedstock is not mixed with acid.

* * * * *